US007288663B2

(12) United States Patent
Kirchmeyer et al.

(10) Patent No.: US 7,288,663 B2
(45) Date of Patent: Oct. 30, 2007

(54) PROCESS FOR PREPARING LINEAR ORGANIC OLIGOMERS

(75) Inventors: Stephen Kirchmeyer, Leverkusen (DE); Sergei Ponomarenko, Moskau (RU)

(73) Assignee: H.C. Starck GmbH (DE)

( * ) Notice: Subject to any disclaimer, the term of this patent is extended or adjusted under 35 U.S.C. 154(b) by 744 days.

(21) Appl. No.: 10/687,148

(22) Filed: Oct. 16, 2003

(65) Prior Publication Data

US 2004/0138476 A1 Jul. 15, 2004

(30) Foreign Application Priority Data

Oct. 18, 2002 (DE) ................ 102 48 876

(51) Int. Cl.
C07D 409/00 (2006.01)
H01L 29/08 (2006.01)
H01L 51/40 (2006.01)
C08F 28/06 (2006.01)
C30B 28/06 (2006.01)

(52) U.S. Cl. ............... 549/59; 257/40; 438/99; 526/256; 117/84

(58) Field of Classification Search ............ 549/59; 257/40; 438/99; 526/256; 428/690; 117/84
See application file for complete search history.

(56) References Cited

U.S. PATENT DOCUMENTS

| 5,347,144 | A | 9/1994 | Garnier et al. | 257/40 |
|---|---|---|---|---|
| 5,546,889 | A | 8/1996 | Wakita et al. | 117/84 |
| 6,107,117 | A | 8/2000 | Bao et al. | 438/99 |
| 6,716,995 | B2 * | 4/2004 | Huang et al. | 549/62 |
| 6,825,358 | B2 * | 11/2004 | Afzali-Ardakani et al. | 549/59 |
| 6,878,801 | B2 * | 4/2005 | Fujiki et al. | 528/380 |
| 6,936,190 | B2 * | 8/2005 | Yoshida | 252/511 |
| 7,102,017 | B2 * | 9/2006 | Liu et al. | 549/59 |
| 2002/0177679 | A1 | 11/2002 | Uckert et al. | 526/259 |
| 2004/0186255 | A1 | 9/2004 | Uckert et al. | 526/259 |
| 2004/0219391 | A1 | 11/2004 | Uckert et al. | 428/690 |

FOREIGN PATENT DOCUMENTS

| EP | 402 269 | 12/1990 |
|---|---|---|
| JP | 02 250 881 | 10/1990 |
| JP | 04 133351 | 5/1992 |

OTHER PUBLICATIONS

M.J. Marsella, T.M. Swager: "Designing Conducting Polymer-Based Sensors: Selective Ionochromic Response in Crown Ether Containing Polythiphenes" J. Am. Chem. Soc., Bd. 115, No. 25, 1993, Seiten 12214-12215, XP002298832.
Database Beilstein Beilstein Institute for Organic Chemistry, Frankfurt-Main, DE; XP002298835 Database accession No. 8383510 Zusammenfassung & D. Hirayama et al.: Chem. Lett. Nr. 5 2000, Seiten 570-571.
Database Beilstein Beilstein Institute for Organic Chemistry, Frankfurt-Main, DE; XP002298836 Database accession No. 2831607, 3116450, 3115137 Zusammenfassung & T. Kauffmann et al.: Chem. Ber., Bd. 116, Nr. 2, 1983, Seiten 479-491.
Database Beilstein Beilstein Institute for Organic Chemistry, Frankfurt-Main, DE; XP002298837 Database accession No. 4508336, 4508397, 4509578, 4509924, 4509933, 4510374 Zusammenfassung & U. Dahlmann, R. Neidlein: Helv. Chim. Acta, Bd. 79, 1996, Seiten 755-766.
Database Beilstein Beilstein Institute for Organic Chemistry, Frankfurt-Main, DE; XP002298838 Database accession No. 2818027 Zusammenfassung & T. Sone et al.: Chem. Lett., 1982, Seiten 1195-1198.
B.H. Lipshutz et al.: , "Inter-and Intramolecular Biaryl Couplings Via Cyanocuprate Intermediates" Tetrahedron Lett., Bd. 35, No. 6, 1994, Seiten 815-818, XP002298833 Tabelle 1.
R.G. Hicks, M.B. Nodwell: "Synthesis and Electronic Structure Investigations of .alpha.,.omega, -Bis(arylthio)oligothiophenes: Toward Understanding Wire-Linker Interactions in Molecular-Scale Electronic Materials" J. Am. Chem. Soc., Bd. 122, No. 28, 2000, Seiten 6746-6753, XP002298834 Scheme 1 and 3.
M.R. Andersson et al.: "Substituted polythiophenes designed for optoelectronic devices and conductors" J. Mater. Chem., Bd. 9, 1999, Seiten 1933-1940, XP002230638 das ganze Dokument.
M. Sato, M. Hiroi: "Preparation of Long Alkyl-substituted Oligothiophenes" Chem. Lett., 1994, Seiten 985-988, XP9005709 das ganze Dokument.
P.F. Van Hutten et al.: "Structure of Thiophene-Based Regioregular Polymers and Block Copolymers and Its Influence on Luminescence Spectra" J. Phys. Chem., Bd. 99, No. 10, 1995, Seiten 3218-3224, XP2091472 das ganze Dokument.
P. Bäuerle et al.: "Synthesis and Structural Characterization of Alkyl Oligothiophenes—The First Iosmerically Pure Dialkylsexithiophene" J. Chem. Soc. Perkin Trans. 2, 1993, Seiten 489-494, XP9005708 das ganze Dokument.

(Continued)

Primary Examiner—Deborah C. Lambkin
(74) Attorney, Agent, or Firm—Connolly Bove Lodge & Hutz LLP

(57) ABSTRACT

The present invention relates to a process for preparing compounds of the formula (I),

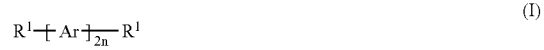

where
n is an integer from 2 to 5,
$R^1$ is H or a $C_1$-$C_{20}$-alkyl group which may be interrupted by one or more O or S atoms, silylene, phosphonoyl or phosphoryl groups and
Ar is substituted or unsubstituted 1,4-phenylene, 2,7-fluorene or 2,5-thiophene, with Ar being able to be identical or different,
semiconductive layers comprising these compounds and their use in semiconductor technology.

13 Claims, No Drawings

OTHER PUBLICATIONS

Adv. Mater. Jan. 16, 2002, 14, No. 2, Dimitrakopoulos, Chritos D. and Malenfant, Patrick R.L.; "Organic Thin Film Transistors for Large area Electronics" pp. 99-117.

J. Am. Chem. Soc. 1993, 115, pp. 12214-12215; Marsella, Michael J. and Swager, Timothy M.; "Designing Conducting Polymer-Based Sensors: Selective Ionochromic Response in Crown Ether Containing Polythiophenes"—Supplementary Material, pp. 1-3.

Chem. Mater. 1995, 7, pp. 2235-2237; H.E. Katz, L. Torsi, and A. Dodabalapur, "Synthesis, Material Properties, and Transistor Performance of Highly Pure Thiophene Oligomers".

Heterocycles, vol. 20, No. 10, 1983, Jacques Kagan and Sudershan K. Arora; "The Synthesis of Alpha-Thiophene Oligomers by Oxidative Coupling of 2-Lithiothiophenes" pp. 1937-1940.

Synthesis; Nov. 1993, Institut für Organische Chemie der Univesität Stuttgart, Peter Bäuerle, Frank Würthner, Günther Götz, Franz Effenberger; "Selective Synthesis of α-Substituted Oligothiophenes" pp. 1099-1103.

Chem. Mater. 1993, 5, Gianni Zotti and Gilberto Schiavon; "Thiophene Oligomers as Polythiophene Models. 1. Anodic Coupling of Thiophene Oligomers to Dimers: A Kinetic Investigation" pp. 430-436.

* cited by examiner

PROCESS FOR PREPARING LINEAR ORGANIC OLIGOMERS

BACKGROUND OF THE INVENTION

1. Field of the Invention

The invention relates to a process for preparing linear organic oligomers, semiconductive layers comprising these oligomers and their use in semiconductor technology.

2. Brief Description of the Prior Art

The field of molecular electronics has developed rapidly in the last 15 years with the discovery of organic conductive and semiconductive compounds. In this time, many compounds which have semiconductive or electrooptical properties have been found. While it is generally accepted that molecular electronics will not displace conventional semiconductor building blocks based on silicon, it is believed that molecular electronic components will open up new applications in which suitability for coating large areas, structural flexibility, processability at low temperatures and low costs are required. Semiconductive organic compounds are at present being developed for applications such as organic field effect transistors (OFETs), organic luminescence diodes (OLEDs), sensors and photovoltaic elements. Simple structuring and integration of OFETs into integrated organic semiconductor circuits make it possible to achieve inexpensive solutions for smart cards or price signs which have hitherto not been able to be realized by means of silicon technology because of the price and the lack of flexibility of the silicon building blocks. Likewise, OFETs could be used as switching elements in large-area flexible matrix displays.

In organic field effect transistors, two large classes of compounds have hitherto been used. All of these compounds have long conjugated units and are divided according to molecular weight and structure into conjugated polymers and conjugated oligomers. Here, oligomers are generally distinguished from polymers on the basis of oligomers having a uniform molecular structure and a molecular weight of less than 10000 dalton, and polymers generally having a molecular weight distribution. However, there is a continuous transition between oligomers and polymers. The distinction between oligomers and polymers also often reflects the difference in the processing of these compounds. Oligomers are frequently vaporizable and can be applied to substrates by vapour deposition processes. Compounds which are no longer vaporizable and therefore have to be applied by other processes are frequently referred to as polymers, regardless of their molecular structure.

An important prerequisite for preparing high-quality organic semiconductor circuits is compounds of extremely high purity. Related to this prerequisite is the fact that in semiconductors, ordering phenomena play a major role. Hindrance of a uniform alignment of the compounds and formation of pronounced grain boundaries lead to a dramatic deterioration in the semiconductor properties. As such, organic semiconductor circuits which have been built up using compounds which do not have an extremely high purity are generally unusable. Residual impurities can, for example, inject charges into the semiconductive compound ("doping") and thus decrease the On/Off ratio or can serve as charge scavengers and thus drastically reduce the mobility. Furthermore, impurities can initiate reaction of the semiconductive compounds with oxygen and oxidizing impurities can oxidize the semiconductive compounds and thus decrease possible storage, processing and operating lives.

Vaporizable compounds generally have the advantage that further purification occurs during the vaporization step and impurities which are difficult to vaporize are not applied. However, contamination by small amounts of other compounds which are very similar to the desired compounds and vaporize in a similar way cannot be eliminated in this way. It is therefore, in particular, necessary to provide vaporizable compounds which do not contain such impurities.

Important representatives of oligomeric semiconductive compounds are, for example, oligothiophenes, in particular those having terminal alkyl substituents (Adv. Mater., 2002, Volume 14, p. 99). The use of such oligothiophenes for producing organic field effect transistors is described, for example, in WO-A 92/01313 and JP-A 04 133 351.

There have been a series of attempts to prepare oligothiophenes of sufficient purity. Thus, EP-A 402 269 describes the preparation of oligothiophenes by oxidative coupling, for example using iron chloride (p. 7, lines 20-30, p. 9, lines 45-55).

However, this synthetic method leads to oligothiophenes which are present in the cationic form, also referred to among specialists as the doped form (EP-A 402 269, p. 8, lines 28-29). These oligothiophenes are as a result unusable for applications in semiconductor electronics, since the cationic form of the oligothiophenes conducts electric current well but displays no semiconductor effect. Although it is possible to reduce cationic oligothiophenes, e.g. by means of an electrochemical or chemical reaction, this is complicated and does not lead to the desired result.

An alternative is the coupling of organolithium compounds using iron(III) salts, e.g. iron(III) chloride. This reaction generally gives undoped, i.e. uncharged, oligothiophenes, but secondary reactions accompanying this reaction lead to products which are heavily contaminated with iron and chlorine. Iron(III) compounds other than iron(III) chloride, for example iron(III) acetylacetonate, have been proposed as coupling reagents (J. Am. Chem. Soc., 1993, 115, 12214). However, owing to the lower reactivity of this coupling reagent, this variant has the disadvantage that the reaction has to be carried out at elevated temperature. The higher temperature promotes lithium-hydrogen exchange and the secondary reactions occurring as a result make it impossible to obtain high-quality oligothiophenes even by means of intensive purification operations (Chem. Mater., 1995, 7, 2235).

Syntheses using Grignard compounds (JP-A 02 250 881) or organozinc compounds (U.S. Pat. No. 5,546,889) in the presence of nickel catalysts likewise lead to products which have to be purified at high cost.

A further possible way of preparing oligothiophenes which has been described in the literature is oxidative coupling by means of copper salts, in particular by means of copper(II) chloride. Thus, Kagan et al. describes the oxidative coupling of 2-lithiothiophenes in the presence of copper (II) chloride in dimethylformamide/tetrahydrofuran (Heterocycles, 1983, 20, 1937). Some improvements in the procedure, e.g. the use of complexed lithium alkyl compounds as lithiation reagents, have been proposed. However, it has been found in the preparation of, for example, sexithiophene that the product still contains 0.77% by weight of chlorine and 0.033% by weight of copper after purification by recrystallization. Of these impurities, at least the chlorine is at least partly chemically bound to the oligothiophene and cannot be removed further even by means of further complicated purification (Katz et al., Chem. Mater., 1995, 7, 2235).

There is therefore a continuing need for an improved process for preparing organic oligomers, in particular oligothiophenes, which have only very small amounts of contamination and thus few defects. In particular, there is a need for such processes for preparing organic oligomers which give the oligomers in high quality for use as semiconductors without additional complicated purification operations.

It is therefore an object of the present invention to provide such a process.

SUMMARY OF THE INVENTION

It has surprisingly been found that coupling of appropriately lithiated starting compounds using copper(II) chloride makes it possible to obtain organic oligomers, in particular oligothiophenes, in significantly improved yield and quality when the coupling, using a copper(II) compound, is carried out with the organolithium precursor to be coupled being present in dissolved form prior to addition of the copper(II) compound.

The present invention accordingly provides processes for preparing compounds of the formula (I),

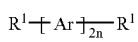

(I)

where n is an integer from 2 to 5, preferably 2 or 3, $R^1$ is H or a $C_1$-$C_{20}$-alkyl group, preferably a $C_1$-$C_{12}$-alkyl group, which may be interrupted by one or more O or S atoms, silylene, phosphonoyl or phosphoryl groups and Ar is substituted or unsubstituted 1,4-phenylene, 2,7-fluorene or 2,5-thiophene, with Ar being able to be identical or different but preferably being identical, characterized in that, compounds of the formula (II),

(II)

where n, $R^1$ and Ar are as defined for the formula (I), are completely dissolved in an organic solvent or solvent mixture at a temperature of from –100° C. to +20° C. and are coupled with one another at temperatures of from –100° C. to +20° C. with the aid of one or more copper(II) compound(s).

DETAILED DESCRIPTION OF THE INVENTION

Possible substituents of Ar are, for example, linear or branched $C_1$-$C_{20}$-alkyl radicals, preferably $C_1$-$C_{12}$-alkyl radicals, or linear $C_1$-$C_{20}$-alkyl radicals which are interrupted by one or more O atoms. Any substituents (one or more) present on the 2,7-fluorene units are preferably located in the 9-position.

The process of the invention is preferably a process for preparing compounds of the formula (I-a),

(I-a)

where n is an integer from 2 to 4, preferably 2 or 3, $R^1$ is H or a $C_1$-$C_{20}$-alkyl group, preferably a $C_1$-$C_{12}$-alkyl group, which may be interrupted by one or more O or S atoms, silylene, phosphonoyl or phosphoryl groups and $R^2$, $R^3$ are each, independently of one another, H or a substituted or unsubstituted $C_1$-$C_{20}$-alkyl group, a substituted or unsubstituted $C_1$-$C_{20}$-alkoxy group or together form a substituted or unsubstituted $C_1$-$C_6$-dioxyalkylene group, preferably each, independently of one another, H or a $C_1$-$C_6$-alkyl group, particularly preferably H, characterized in that compounds of the formula (II-a)

(II-a)

where n, $R^1$, $R^2$ and $R^3$ are as defined for the formula (I-a), are completely dissolved in an organic solvent or solvent mixture at a temperature of from –100° C. to +20° C. and coupled with one another at temperatures of from –100° C. to +20° C. with the aid of one or more copper(II) compound(s).

Suitable substituents for $R^2$ and $R^3$ are in principle substituents which do not react with organolithium compounds under the prevailing reaction conditions, for example linear or branched, substituted or unsubstituted $C_1$-$C_{20}$-alkyl radicals, substituted or unsubstituted $C_5$-$C_{12}$-cycloalkyl radicals, substituted or unsubstituted $C_6$-$C_{14}$-aryl radicals.

In the context of the invention, $C_1$-$C_{20}$-alkyl radicals represent, for example, methyl, ethyl, n-propyl or isopropyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl or n-octadecyl, $C_5$-$C_{12}$-cycloalkyl radicals represent, for example, cyclopentyl, cyclohexyl, cycloheptyl, cyclooctyl, cyclononyl, cyclodecyl, $C_6$-$C_{14}$-aryl radicals represent, for example, phenyl, o-, m-, p-tolyl, benzyl, 2,3-, 2,4-, 2,5-, 2,6-, 3,4-, 3,5-xylyl, mesityl or naphthyl. The above list serves as an exemplary explanation of the invention and is not to be considered as definitive.

Suitable organic solvents are in principle all solvents or solvent mixtures which do not react with organolithium compounds, for example those of the formula (II) or (II-a) or further compounds mentioned in this patent application. These are generally compounds which bear no halogen atoms or hydrogen atoms which are reactive towards organolithium compounds. Suitable solvents are, for example, alkanes such as pentane, hexane and heptane, aromatics such as benzene, toluene and xylenes and also compounds containing ether groups, e.g. diethyl ether, tert-butyl methyl ether, dioxane and tetrahydrofuran. In the process of the invention, preference is given to using solvents containing ether groups. Very particular preference is given to tetrahydrofuran. However, it is also possible for the solvent used to be a mixture of two or more of these solvents. For example, mixtures of the preferably used solvent tetrahydrofuran with alkanes, e.g. hexane (e.g. present in commercially available solutions of starting materials such as organolithium compounds) can be used. For the purposes of the invention, it is important that the solvent, the solvents or their mixtures are chosen so that the compounds of the formula (II) or (II-a) are present in dissolved form prior to addition of the copper(II) compound.

As copper(II) compounds, it is possible to use, for example, copper(II) halides, preferably copper(II) chloride, copper(II) bromide or copper(II) iodide, or compounds which are at least partially soluble in the abovementioned solvents, for example a copper(II) salt of a carboxylic acid or sulphonic acid, preferably copper(II) acetate, copper(II) citrate, copper(II) acetylacetonate, copper(II) glycinate, copper(II) methylsulphonate, copper(II) trifluoromethanesulphonate or copper(II) toluenesulphonate or a copper(II) alkoxide, preferably copper(II) methoxide, copper(II) ethoxide, or mixtures of these in the process of the invention. Preference is given to using copper(II) chloride.

The copper(II) compounds are used as coupling reagents in the process of the invention. They are added in crystalline, dissolved or partly dissolved form to the reaction solution. They are preferably used in their anhydrous form. They can be added a little at a time or all at once. Copper(II) chloride is preferably added all at once in crystalline anhydrous form. The copper(II) compounds can be used either in an equimolar ratio to the compounds of the formula (II) or (II-a) or in excess.

The compounds of the formula (II) or (II-a) can either be used in isolated form or can be prepared directly in the reaction solution ("in situ") and used without further work-up. The "in-situ" preparation is preferred for economic reasons.

A preferred embodiment of the process of the invention is therefore one in which the compounds of the formula (II) are prepared by reaction of compounds of the formula (III),

where n, $R^1$ and Ar are as defined above and

X is H, Cl, Br or I, with an organolithium compound at a temperature of from −100° C. to +20° C. in an organic solvent, where the reaction mixture is stirred further, if appropriate at or after heating to a temperature of from −20° C. to +40° C., and is subsequently cooled back down to a temperature of from −100° C. to +20° C. and the copper(II) compound is added without further work-up.

In carrying out the above-described preferred embodiment, it is also possible for the reaction mixture firstly to be stirred further at a temperature of from −100° C. to +20° C., then to be heated to a temperature of from −20° C. to +40° C. and subsequently to be cooled back down to a temperature of from −100° C. to +20° C. In the overlap of the temperature ranges in the above-described preferred embodiment, it should be recognised that in order to be able to heat to a particular temperature, the temperature must have previously been lower than this. This proviso applies for each temperature of the overlapping range between "from −100° C. to +20° C." and "from −20° C. to +40° C.", i.e. for every temperature in the range from −20° C. to +20° C.

In a particularly preferred embodiment of the process of the invention, the compounds of the formula (III) are compounds of the formula (III-a)

where n, $R^1$, $R^2$ and $R^3$ are as defined above and

X is H, Cl, Br or I, but preferably H.

Suitable organolithium compounds are, for example, organolithium compounds such as alkyllithium compounds, e.g. n- or tert-butyllithium, methyllithium or lithium compounds having other alkyl radicals which may, if desired, be modified prior to the reaction in order to reduce their reactivity and to suppress secondary reactions, for example alkylations. Such modification can be achieved, for example, by reacting the alkyllithium compounds with amines so as to form lithium amides. Amines suitable for this purpose contain at least one hydrogen-nitrogen bond. These are, for example, dimethylamine, diethylamine, dipropylamine, diisopropylamine, dibutylamine, methylethylamine, methylpropylamine, methylbutylamine, ethylpropylamine and ethylbutylamine. A further possible method of modification is complexation of the alkyllithium compound, e.g., by means of tetramethylethylenediamine.

Preference is given to using lithium amides, preferably lithium diisopropylamide, or a complexed or uncomplexed alkyllithium compound, preferably n- or tert-butyllithium or methyllithium.

Solvents suitable for the preparation of compounds of the formula (II) or (II-a) are in principle the same solvents or solvent mixtures described above for the subsequent coupling reaction. In the "in-situ" preparation of the compounds of the formula (II) or (II-a), preference is given to either the use of the same solvent or merely an addition of one or more further solvents.

The coupling reaction is initiated at temperatures of from −100° C. to +20° C., preferably from −80° C. to −60° C., by addition of the copper(II) compound. After addition of the copper(II) compound, the reaction mixture is stirred further at a temperature of from −100° C. to +20° C. for a period of, for example, from 5 minutes to 5 hours, if appropriate even longer. It may then be necessary to complete the coupling reaction by further reaction at temperatures of from −80° C. to +40° C. For example, it is possible for the temperature of the reaction mixture firstly to be increased slowly and the reaction finally to be completed by further stirring at a higher temperature. The time required to complete the coupling reaction is dependent on the temperature selected. The completeness of the reaction can be checked by simple methods, for example thin layer chromatography. When the reaction conditions are chosen appropriately, the coupling reaction proceeds essentially to completion. For the purposes of the invention, the coupling reaction is essentially complete when no further conversion can be observed. This is independent of the molar amount of starting compounds reacted.

The reaction mixture is worked up by methods known per se, e.g. by dilution, precipitation, filtration, extraction, washing, recrystallization from suitable solvents, chromatography and/or sublimation. For example, the work-up can be carried out by pouring the reaction mixture after the reaction is complete into a mixture of acidified water or ice water, e.g. prepared from water or ice water and 1 M HCl in a volume ratio of 20:1, and diethyl ether, separating off the organic phase, washing it with water, filtering off the product obtained as a solid, washing this with diethyl ether and subsequently drying it under reduced pressure. The compounds of the formula (I) or (II-a) are semiconductive and can be obtained in high quality and purity even without further subsequent purification operations and contain only small amounts of impurities, e.g. 0.5% by weight or less of chlorine, preferably 0.3% by weight or less of chlorine, particularly preferred even 0.03% by weight or less of chlorine and/or 0.1% by weight or less of copper, preferably even 0.02% by weight or less of copper. However, it is possible to purify these products further by known methods, e.g. by recrystallization, chromatography or sublimation.

The process of the invention thus makes it possible for the first time to prepare organic oligomers, which for the purposes of the invention are compounds of the formula (I) or (I-a), in particular oligothiophenes, containing only very small amounts of impurities and thus having few defects without complicated purification processes. Surprisingly, the process of the invention does not display the disadvantages of the process described by Kagan (Heterocycles, 1983, 20, 1937), namely the continuing presence, despite purification by recrystallization, of 0.77% by weight of chlorine as impurity, of which at least part is chemically bound to the oligothiophene and cannot be removed again even by further complicated purification (Chem. Mater., 1995, 7, 2235).

A further advantage of the process of the invention over that of Kagan et al. is that an "in-situ" preparation, in particular of the preferred compounds of the formula (II) or (II-a), is possible since no excess of the compounds of the formula (III) or (III-a) is necessary. Kagan et al. use a two-fold excess of thiophene, since otherwise they observe the formation of considerable amounts of undesirable by-products (e.g. dimers) which can be separated from the desired product only with difficulty. However, the excess thiophene has to be removed prior to the coupling reaction, which not only means additional cost but also leads to a loss of 15% of the thiophene used in excess (Heterocycles, 1983, 20, 1937).

Furthermore, the compounds of the formula (I) or (I-a) can be prepared largely free of oligomers having a higher or lower molecular weight by means of the process of the invention, which dispenses with the complicated purification of difficult-to-separate mixtures.

The compounds of the formula (I) or (I-a) prepared by the process of the invention are uncharged and semiconductive and, due to their purity, are particularly well-suited for use as semiconductors in active and light-emitting electronic components such as field effect transistors, organic luminescence diodes, photovoltaic cells, lasers or sensors. To use the compounds of the formula (I) or (I-a) prepared according to the invention, they are applied in the form of layers to suitable substrates, for example to silicon wafers, polymer films or glass sheets provided with electrical or electronic structures. All application processes known to those skilled in the art are in principle possible for application of the compounds. For example, the compounds of the formula (I) or (I-a) can be applied from solution, with the solvent subsequently being evaporated. Application from solution can be carried out by known methods, for example by spraying, dipping, printing and doctor blade coating, spin-coating and by ink jet printing. The compounds of the formula (I) or (I-a) can likewise be applied from the gas phase, e.g. by vapour deposition.

The present invention therefore also provides layers comprising, preferably consisting essentially of, compounds of the formula (I)

(I)

where n, $R^1$ and A are as defined above, characterized in that they contain 0.5% by weight or less of chlorine, preferably 0.3% by weight or less of chlorine, particularly preferred 0.03% by weight or less of chlorine, and are semiconductive.

For the purposes of the invention, 0.5% by weight or less of chlorine, 0.3% by weight or less of chlorine and 0.03% by weight or less of chlorine mean from 0% by weight to 0.5% by weight of chlorine, from 0% by weight to 0.3% by weight of chlorine and from 0% by weight to 0.03% by weight of chlorine, respectively. Any chlorine impurities present can be either or both chemically bound chlorine or/and chlorine which is not chemically bound, for example in the form of chlorine compounds such as chlorine salts.

These layers are preferably layers in which the compounds of the formula (I) are compounds of the formula (I-a),

where n, $R^1$, $R^2$ and $R^3$ are as defined above.

In particularly preferred embodiments, the layers are layers which are suitable for use in active and light-emitting electronic compounds such as field effect transistors, organic luminescence diodes, photovoltaic cells, lasers or sensors.

The layers of the invention can be further modified after application, for example by means of heat treatment, e.g. with the layers passing through a liquid-crystalline phase, or for structuring, e.g. by laser ablation.

The invention is further described by way of the following non-limiting examples.

EXAMPLES

5-Hexyl-2,2':5',2''-terthiophenes and 5-ethyl-2,2':5',2''-terthiophenes were prepared by known methods (Synthesis, 1993, p. 1099; Chem. Mater., 1993, Volume 5, p. 430).

All reaction vessels were baked and flooded with nitrogen using customary protective gas techniques before use.

Example 1

Preparation of 5,5'''''-dihexyl-2,2':5',2'':5'',2''':5''',2'''': 5'''',2'''''-sexithiophene (I-a-1)

1.2 ml of n-butyllithium (BuLi, 2.5 molar (M) solution in hexane, 3 mmol) were added at −78° C. to 10 ml of absolute tetrahydrofuran (abs. thf) under nitrogen. A solution of 334 mg of diisopropylamine (3.3 mmol) in 5 ml abs. thf was subsequently added over a period of 5 minutes and the mixture was stirred for a further 5 minutes. A solution of 1.0 g of 5-hexyl-2,2':5',2''-terthiophene (3 mmol) in 20 ml of abs. thf was then added dropwise over a period of 20 minutes, after which no precipitate and no turbidity could be observed in the clear yellow solution. The reaction solution was stirred at −78° C. for 30 minutes and subsequently allowed to come to 0° C. After cooling back down to −78° C., 404 mg of $CuCl_2$ (3 mmol) were added all at once to the clear, yellow solution and the mixture was stirred at −78° C. for one hour. The cold bath (acetone/dry ice) was removed and the temperature of the reaction mixture was then slowly allowed to come to room temperature (23° C.). After stirring for another 16 hours at room temperature, the reaction mixture was poured into 200 ml of diethyl ether, and a mixture of 200 ml of deionized (distilled) water and 10 ml of 1 M HCl was added. The organic phase, which contained an orange precipitate, was separated off, washed with distilled water and filtered. The precipitate which had been filtered off was washed with abs. diethyl ether and dried under reduced pressure. This gave 605 mg (61% of theory) of the product in the form of an orange powder. According to elemental analysis, the product contained 0.02% by weight of chlorine and 0.014% by weight of copper.

FD MS analysis: M.+ 100%, m/e=662.2 Melting behaviour (° C.): K 297 SmX 304 N 312 I (K=crystalline, SmX=smectic liquid-crystalline, N=nematic liquid-crystalline, I=isotropic liquid; the numerical values between the phase designations indicate the transition temperature in ° C., e.g. K 297 SmX=transition from the crystalline state to the smectic liquid-crystalline state at 297° C.) (melting behaviour determined by DSC (differential scanning calorimetry) Mettler TA-4000 Thermosystem, Scanning rate 1K/min)

Example 2

Preparation of 5,5'''''-dihexyl-2,2':5',2'':5'',2''':5''',2'''': 5'''',2'''''-sexithiophene (1-a-2)

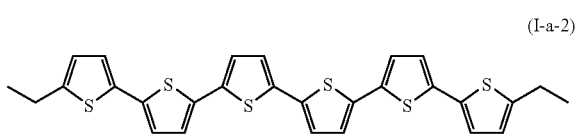

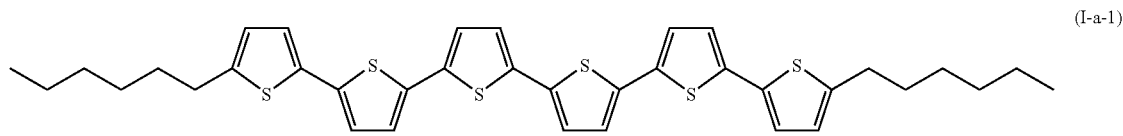

0.8 ml of n-butyllithium (BuLi, 2.5 molar (M) solution in hexane, 2 mmol) was added at −78° C. to 10 ml of absolute tetrahydrofuran (abs. thf) under nitrogen. A solution of 223 mg of diisopropylamine (2.2 mmol) in 5 ml abs. thf was subsequently added dropwise over a period of 5 minutes and the mixture was stirred for a further 5 minutes. A solution of 553 mg of 5-ethyl-2,2':5',2''-terthiophene (2 mmol) in 20 ml of abs. thf were then added dropwise over a period of 10 minutes, after which no precipitate and no turbidity could be observed in the clear yellow solution. The reaction solution was stirred at −75° C. for 30 minutes and subsequently allowed to come to 0° C. After cooling back down to −78° C., 538 mg of $CuCl_2$ (4 mmol) were added all at once to the clear, yellow solution and the mixture was stirred at −78° C. for 10 minutes. The cold bath (acetone/dry ice) was removed and the temperature of the reaction mixture was then slowly allowed to come to room temperature (23° C.). After stirring for another one hour at room temperature, the reaction mixture was poured into 200 ml of diethyl ether, and a mixture of 200 ml of ice water and 10 ml of 1 M HCl was added. The organic phase, which contained an orange precipitate, was separated off, washed with distilled water and filtered. The precipitate which had been filtered off was washed with abs. diethyl ether and dried to constant weight under reduced pressure. This gave 422 mg (77% of theory) of the product in the form of an orange powder. According to elemental analysis, the product contained 0.13-0.14% by weight of chlorine.

FD MS analysis: M.+ 100%, m/e=550.1 Melting behaviour (° C.): K 300 I (K=crystalline, I=isotropic liquid)

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing compounds of the formula (I),

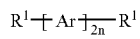
(I)

where n is an integer from 2 to 5, $R^1$ is H or a $C_1$-$C_{20}$-alkyl group optionally interrupted by one or more O or S atoms, silylene, phosphonoyl or phosphoryl groups and Ar is substituted or unsubstituted 1,4-phenylene, 2,7-fluorene or 2,5-thiophene, with Ar being able to be identical or different, comprising completely dissolving compounds of the formula (II),

(II)

where n, $R^1$ and Ar are as defined for the formula (I), in an organic solvent or solvent mixture at a temperature of from −100° C. to +20° C. and coupling with one another at temperatures of from −100° C. to +20° C. with the aid of one or more copper(II) compound(s).

2. Process for preparing compounds of the formula (I-a),

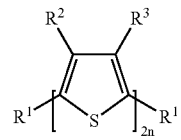
(I-a)

where n is an integer from 2 to 4, $R^1$ is H or a $C_1$-$C_{20}$-alkyl group optionally interrupted by one or more O or S atoms, silylene, phosphonoyl or phosphoryl groups and $R^2$, $R^3$ are each, independently of one another, H or a substituted or unsubstituted $C_1$-$C_{20}$-alkyl group, a substituted or unsubstituted $C_1$-$C_{20}$-alkoxy group or together form a substituted or unsubstituted $C_1$-$C_6$-dioxyalkylene group, comprising completely dissolving compounds of the formula (II-a)

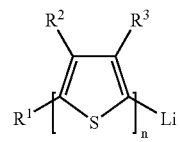
(II-a)

where n, $R^1$, $R^2$ and $R^3$ are as defined for the formula (I-a), in an organic solvent or solvent mixture at a temperature of from −100° C. to +20° C. and coupling with one another at temperatures of from −100° C. to +20° C. with the aid of one or more copper(II) compound(s).

3. Process according to claim 1, characterized in that n is 2 or 3.

4. Process according to claim 1, characterized in that $R^1$ is a $C_1$-$C_{12}$-alkyl group.

5. Process according to claim 2, characterized in that $R^2$ and $R^3$ are each, independently of one another, H or a $C_1$-$C_6$-alkyl group.

6. Process according to claim 2, characterized in that $R^2$ and $R^3$ are each H.

7. Process according to claim 1, characterized in that alkanes, aromatics or compounds containing ether groups or mixtures of two or more of these compounds are used as solvent.

8. Process according to claim 1, characterized in that tetrahydrofuran or a mixture of tetrahydrofuran with alkanes is used as solvent.

9. Process according to claim 1, characterized in that the compounds of the formula (II) are prepared by reacting compounds of the formula (III),

(III)

where n, R¹ and Ar are as defined in claim 1, and
X is H, Cl, Br or I,
with an organolithium compound at a temperature of from −100° C. to +20° C. in an organic solvent,
where the resulting reaction mixture is stirred further, optionally at or after heating to a temperature of from −20° C. to +40° C., and is subsequently cooled back down to a temperature of from −100° C. to +20° C. and the copper(II) compound is added without further work-up.

10. Process according to claim 9, characterized in that the compounds of the formula (III) are compounds of the formula (III-a),

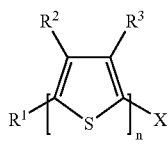

(III-a)

wherein n is an integer from 2 to 5,

R¹ is H or a $C_1$-$C_{20}$-alkyl group optionally interrupted by one or more O or S atoms, silylene, phosphonoyl or phosphoryl groups and R² and R³ are each, independently of one another, H or a substituted or unsubstituted $C_1$-$C_{20}$-alkyl group, a substituted or unsubstituted $C_1$-$C_{20}$-alkoxy group or together form a substituted or unsubstituted $C_1$-$C_6$-dioxyalkylene group and X is H, Cl, Br or I.

11. Process according to claim 9, characterized in that the organolithium compound is a lithium amide, or a complexed or uncomplexed alkyllithium compound.

12. Process according to claim 1, characterized in that the copper(II) compound is a copper(II) halide, a copper(II) salt of a carboxylic acid or sulphonic acid, or a copper(I) alkoxide.

13. Process according to claim 1, characterized in that the reaction mixture is stirred further at temperatures of from −80° C. to +40° C. to complete the coupling reaction.

* * * * *

UNITED STATES PATENT AND TRADEMARK OFFICE
CERTIFICATE OF CORRECTION

PATENT NO. : 7,288,663 B2  Page 1 of 1
APPLICATION NO. : 10/687148
DATED : October 30, 2007
INVENTOR(S) : Stephan Kirchmeyer et al.

It is certified that error appears in the above-identified patent and that said Letters Patent is hereby corrected as shown below:

On the Title Page:

Item [75] In the Inventors:

"Stephen Kirchmeyer" should read -- Stephan Kirchmeyer --.

In the Claims:

In Claim 12, in column 14 and line 17, "or a copper (I)" should read

-- or a copper (II) --.

Signed and Sealed this

Eighteenth Day of March, 2008

JON W. DUDAS
*Director of the United States Patent and Trademark Office*